US010751035B2

(12) United States Patent
White

(10) Patent No.: US 10,751,035 B2
(45) Date of Patent: Aug. 25, 2020

(54) LARGE BORE CLOSURE DEVICE WITH INNER AND OUTER SEALS

(71) Applicant: St. Jude Medical Puerto Rico LLC, Caguas, PR (US)

(72) Inventor: Troy T. White, Maple Grove, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 809 days.

(21) Appl. No.: 13/675,763

(22) Filed: Nov. 13, 2012

(65) Prior Publication Data

US 2013/0123844 A1 May 16, 2013

Related U.S. Application Data

(60) Provisional application No. 61/560,588, filed on Nov. 16, 2011.

(51) Int. Cl.
*A61B 17/00* (2006.01)
*A61B 17/04* (2006.01)
*A61B 17/34* (2006.01)

(52) U.S. Cl.
CPC ...... *A61B 17/0057* (2013.01); *A61B 17/0469* (2013.01); *A61B 2017/00659* (2013.01);
(Continued)

(58) Field of Classification Search
CPC ............ A61B 2017/00663; A61B 2017/00884
See application file for complete search history.

(56) References Cited

U.S. PATENT DOCUMENTS 3,470,875 A 10/1969 Johnson
5,431,666 A 7/1995 Sauer et al.
(Continued)

FOREIGN PATENT DOCUMENTS

EP 0818178 A2 1/1998
EP 1158907 A1 12/2001
(Continued)

OTHER PUBLICATIONS

Notification of Transmittal of the International Search Report and the Written Opinion of the International Searching Authority, or the Declaration for International Application No. PCT/US2012/064768, dated Feb. 19, 2013, (18 pp.).
(Continued)

*Primary Examiner* — Sarah A Simpson
(74) *Attorney, Agent, or Firm* — Dorsey & Whitney LLP

(57) ABSTRACT

A vascular closure system includes a suture carrying portion, a plurality of needles, and an internal sealing member. The suture carrying portion is insertable through a vessel puncture of a vessel and carries first and second suture ends of at least a first suture member. The plurality of needles are extendable through a wall of the vessel adjacent to the vessel puncture and are configured to connect to the first and second suture ends. Withdrawal of the plurality of needles draws the first and second suture ends through the vessel wall. The internal sealing member is configured to advance along the first suture member through the vessel puncture and into the vessel. Applying a withdrawal force to the first and second suture ends draws the internal sealing member against an internal surface of the vessel wall to at least partially seal closed the vessel puncture.

8 Claims, 16 Drawing Sheets

(52) U.S. Cl.
CPC ............... *A61B 2017/00663* (2013.01); *A61B 2017/00884* (2013.01); *A61B 2017/00951* (2013.01); *A61B 2017/0404* (2013.01); *A61B 2017/047* (2013.01); *A61B 2017/0472* (2013.01); *A61B 2017/3484* (2013.01)

(56) References Cited

U.S. PATENT DOCUMENTS

| | | | |
|---|---|---|---|
| 5,520,702 A | 5/1996 | Sauer et al. | |
| 5,545,178 A * | 8/1996 | Kensey | A61B 17/0057 604/15 |
| 5,562,686 A | 10/1996 | Sauer et al. | |
| 5,613,974 A | 3/1997 | Andreas et al. | |
| 5,643,292 A | 7/1997 | Hart | |
| 5,674,231 A | 10/1997 | Green et al. | |
| 5,700,273 A * | 12/1997 | Buelna et al. | 606/148 |
| 5,709,692 A | 1/1998 | Mollenauer et al. | |
| 5,728,114 A | 3/1998 | Evans et al. | |
| 5,766,183 A | 6/1998 | Sauer | |
| 5,860,990 A | 1/1999 | Nobles et al. | |
| 5,972,005 A | 10/1999 | Stalker et al. | |
| 6,036,699 A | 3/2000 | Andreas et al. | |
| 6,048,357 A | 4/2000 | Kontos | |
| 6,059,800 A * | 5/2000 | Hart et al. | 606/144 |
| 6,136,010 A * | 10/2000 | Modesitt et al. | 606/144 |
| 6,355,050 B1 | 3/2002 | Andreas et al. | |
| 6,562,052 B2 | 5/2003 | Nobles et al. | |
| 6,623,509 B2 | 9/2003 | Ginn | |
| 6,641,592 B1 | 11/2003 | Sauer et al. | |
| 6,896,692 B2 | 5/2005 | Ginn et al. | |
| 6,911,034 B2 | 6/2005 | Nobles et al. | |
| 6,932,824 B1 | 8/2005 | Roop et al. | |
| 6,964,668 B2 | 11/2005 | Modesitt et al. | |
| 6,969,397 B2 | 11/2005 | Ginn | |
| 7,001,400 B1 | 2/2006 | Modesitt et al. | |
| 7,083,635 B2 | 8/2006 | Ginn | |
| 7,235,087 B2 | 6/2007 | Modesitt et al. | |
| 7,361,183 B2 | 4/2008 | Ginn | |
| 7,390,328 B2 | 6/2008 | Modesitt | |
| 7,553,319 B2 | 6/2009 | Bagaoisan et al. | |
| 7,601,161 B1 | 10/2009 | Nobles et al. | |
| 7,618,438 B2 | 11/2009 | White et al. | |
| 7,621,937 B2 | 11/2009 | Pipenhagen et al. | |
| 7,686,821 B2 | 3/2010 | Hathaway et al. | |
| 7,731,726 B2 * | 6/2010 | Belhe et al. | 606/144 |
| 7,744,610 B2 | 6/2010 | Hausen | |
| 7,752,853 B2 | 7/2010 | Singh et al. | |
| 7,753,933 B2 | 7/2010 | Ginn et al. | |
| 7,837,696 B2 | 11/2010 | Modesitt et al. | |
| 7,842,047 B2 | 11/2010 | Modesitt et al. | |
| 7,842,048 B2 | 11/2010 | Ma | |
| 7,846,170 B2 | 12/2010 | Modesitt et al. | |
| 7,850,701 B2 | 12/2010 | Modesitt et al. | |
| 7,883,517 B2 | 2/2011 | Pantages et al. | |
| 7,985,240 B2 | 7/2011 | Bagaoisan et al. | |
| 8,029,476 B2 | 10/2011 | Rosenberg et al. | |
| 8,048,092 B2 | 11/2011 | Modesitt et al. | |
| 8,083,768 B2 | 12/2011 | Ginn et al. | |
| 8,192,456 B2 | 6/2012 | Holman et al. | |
| 2005/0070923 A1 * | 3/2005 | McIntosh | 606/139 |
| 2005/0085854 A1 | 4/2005 | Ginn | |
| 2006/0212071 A1 | 9/2006 | Ginn et al. | |
| 2008/0065151 A1 | 3/2008 | Ginn | |
| 2008/0091235 A1 * | 4/2008 | Sirota | A61B 17/0057 606/215 |
| 2009/0054895 A1 * | 2/2009 | Dillon | A61B 17/0057 606/45 |
| 2009/0099578 A1 | 4/2009 | Heneveld et al. | |
| 2009/0306685 A1 * | 12/2009 | Fill | A61B 17/0057 606/148 |
| 2010/0042118 A1 | 2/2010 | Garrison et al. | |
| 2010/0185234 A1 * | 7/2010 | Fortson et al. | 606/213 |
| 2011/0071567 A1 | 3/2011 | Modesitt et al. | |
| 2014/0155937 A1 * | 6/2014 | Shinde | A61B 17/0401 606/232 |

FOREIGN PATENT DOCUMENTS

| | | |
|---|---|---|
| EP | 1327419 A2 | 7/2003 |
| EP | 1349501 A2 | 10/2003 |
| EP | 1677682 A2 | 7/2006 |
| EP | 1972282 A2 | 9/2008 |
| EP | 2147640 A2 | 1/2010 |
| EP | 2298180 A1 | 3/2011 |
| WO | 9703613 | 2/1997 |
| WO | 0051498 | 9/2000 |
| WO | 0078226 A1 | 12/2000 |
| WO | 2010081106 A1 | 7/2010 |

OTHER PUBLICATIONS

Notification of Transmittal of the International Search Report and the Written Opinion of the International Searching Authority, or the Declaration for International Application No. PCT/US2012/066012, dated Feb. 19, 2013, (17 pp.).

Notification of Transmittal of the International Search Report and the Written Opinion of the International Searching Authority, or the Declaration for International Application No. PCT/US2012/064770, dated Feb. 19, 2013, (16 pp.).

U.S. Appl. No. 61/494,345, filed Jun. 7, 2011.

PCT Communication Relating to the Results of the Partial International Search for International Application No. PCT/US2012/041196, dated Sep. 11, 2012.

* cited by examiner

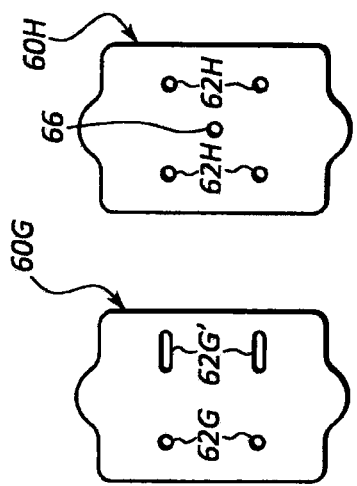
FIG. 20C
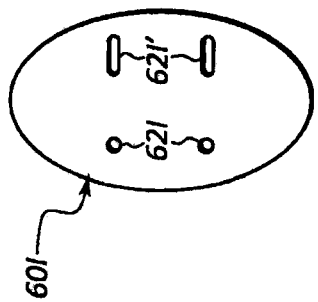
FIG. 20H
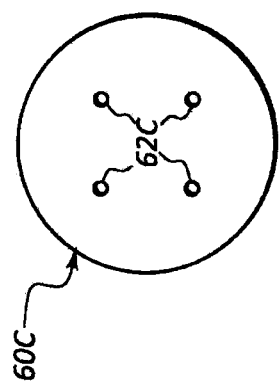
FIG. 20B
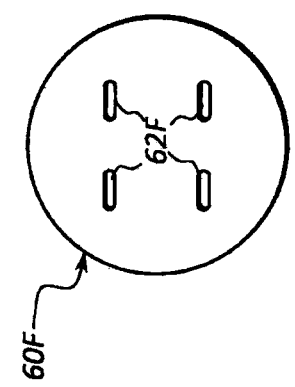
FIG. 20E
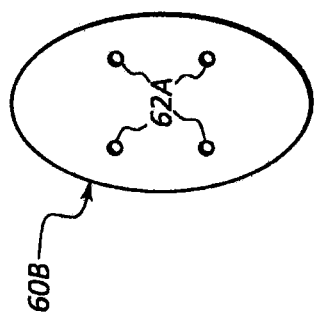
FIG. 20G
FIG. 20I
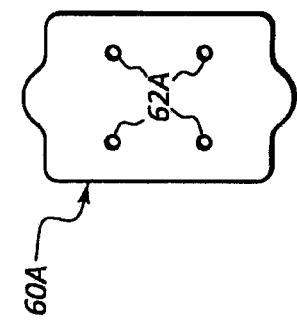
FIG. 20A
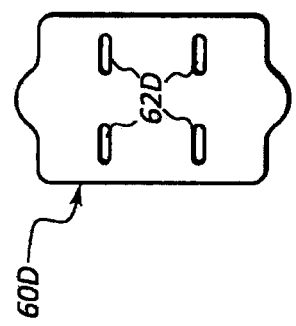
FIG. 20D

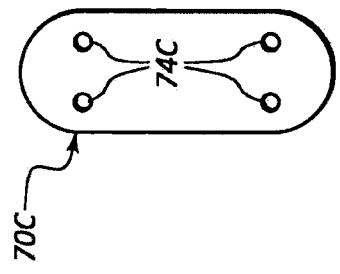
FIG. 21A
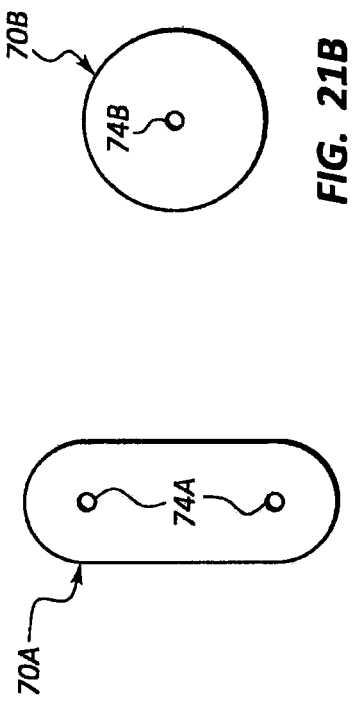
FIG. 21B
FIG. 21D
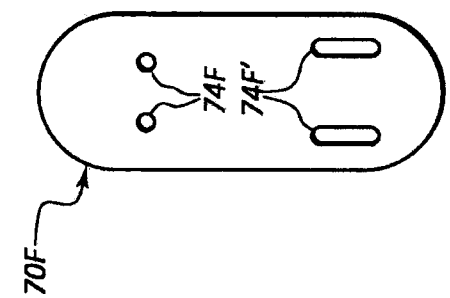
FIG. 21C
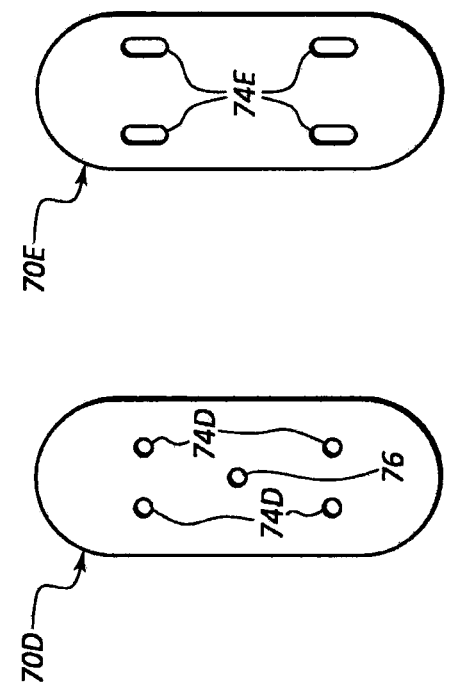
FIG. 21E
FIG. 21F

LARGE BORE CLOSURE DEVICE WITH INNER AND OUTER SEALS

RELATED APPLICATION

This claims the benefit of U.S. Provisional Application No. 61/560,588, filed 16 Nov. 2011, which is hereby incorporated by reference herein in its entirety.

TECHNICAL FIELD

The present disclosure relates to closure devices, and more specifically relates to closure devices that place sutures across an opening in a vessel wall.

BACKGROUND

Various medical procedures, particularly cardiology procedures, involve accessing a corporeal vessel through a percutaneous sheath. The sheath necessarily requires the formation of a hole or opening in the vessel wall so that a medical procedure can be performed via the sheath. After the particular medical procedure has been performed, the sheath must eventually be removed from the vessel and the access hole in the vessel wall must be closed.

A number of prior vascular closure devices have been developed in attempting to provide a solution for the problem of closing a hole in the vessel wall. Tissue approximation typically involves passing a length suture into and through adjacent vessel and subcutaneous tissue, across the vessel opening, and back into and through adjacent vessel and subcutaneous tissue. Certain prior closure devices have involved relatively complicated methods and devices for extracting a length of suture from inside the vessel so that the physician can approximate tissue surrounding the hole in the vessel wall through use of the suture.

U.S. Pat. Nos. 5,643,292 and 6,059,800 disclose example prior suturing devices used for approximating tissue surrounding the opening in a vessel wall. Most prior closure devices enlarge the vessel opening thereby negating the benefits of using smaller or less invasive percutaneous products. Prior suturing devices are also relatively complicated and difficult to use.

There remains a need, therefore, to provide a closure apparatus that effectively places sutures in tissue surrounding an opening in a vessel wall, and seals closed the opening.

SUMMARY

One aspect of the present disclosure relates to a vascular closure system that includes a suture carrying portion, a plurality of needles, and an internal sealing member. The suture carrying portion is insertable through a vessel puncture of a vessel and carries first and second suture ends of at least a first suture member. The plurality of needles are extendable through a wall of the vessel adjacent to the vessel puncture and are configured to connect to the first and second suture ends. Withdrawal of the plurality of needles draws the first and second suture ends through the vessel wall. The internal sealing member is configured to advance along the first suture member through the vessel puncture and into the vessel. Applying a withdrawal force to the first and second suture ends draws the internal sealing member against an internal surface of the vessel wall to at least partially seal closed the vessel puncture.

The vascular closure system may also include an external sealing member configured to advance along the first suture member to a position contacting an outer surface of the vessel wall to at least partially seal closed the vessel puncture. The internal and external sealing members may be connected together with the first suture member. The plurality of needles may connect to the first suture member with at least one suture connector mounted to the first suture member. The vascular closure system may also include an anchor, a handle, and first and second actuators mounted to the handle, wherein the first actuator is operable to expand and retract the anchor within the vessel, and the second actuator is operable to advance and withdraw the plurality of needles.

The vascular closure system may also include a second suture member, wherein the plurality of needles includes two pairs of needles, and a separate one of the two pairs of needles being connecting to one of the first and second suture members. The internal sealing member and external sealing member may each include at least one suture hole sized to receive a portion of the first suture member. The vascular closure system may also include an internal sealing member delivery device configured to retain the internal sealing member in a reduced size configuration and deliver the internal sealing member through the vessel puncture while in the reduced size configuration. The external sealing member may be compacted to seal closed the vessel puncture from outside of the vessel.

Another aspect of the present disclosure relates to a vascular closure device that includes an internal sealing member, at least one suture, and an external sealing member. The internal sealing member is positionable within a vessel. The at least one suture member extends through a vascular puncture in a wall of the vessel at a plurality of locations and through the internal sealing member at a plurality of locations. The at least one suture member is configured to retain the internal sealing member in contact with an inner surface of the vessel at least partially sealing closed the vascular puncture from within the vessel. The external sealing member is configured to advance along the at least one suture member to a position outside of the vessel and at least partially seals closed the vascular puncture from outside the vessel.

The internal sealing member is configured to advance along the at least one suture member, through the vascular puncture, and into the vessel. The at least one suture member may extend through the vascular puncture, and the vascular closure device further comprises a plurality of needles configured to extend through a wall of the vessel adjacent to the vascular puncture, connect to the at least one suture member, and withdraw the at least one suture member through the wall of the vessel at a location separate from the vascular puncture.

The at least one suture member may include a first suture member that extends through a wall of the vessel at multiple locations, extends through the internal sealing member at multiple locations, and extends through the external sealing member at multiple locations. The at least one suture member may extend through the vessel using a suture delivery device that is separate from the at least one sealing member delivery device used to deliver the internal and external sealing members to the vascular puncture.

A further aspect of the present disclosure relates to a method of closing a vascular opening in a wall of a vessel. The method includes providing a vascular closure device having a plurality of needles, at least one suture member, and an internal sealing member. The method also includes positioning first and second ends of the at least one suture member through the vascular opening, drawing the first and second ends of the at least one suture member through the vessel wall at a location adjacent to the vascular opening using the plurality of needles, advancing the internal sealing member along the at least one suture member and through the vascular opening into the vessel, and retaining the internal sealing member against an inner surface of the vessel wall with the at least one suture member to at least partially close the vascular opening.

The method may also include extending the plurality of needles through the vessel wall and connecting the plurality of needles to the first and second ends of the at least one suture member. The method may include advancing an external sealing member along the at least one suture member to a position contacting an outer surface of the vessel wall to at least partially seal closed the vascular opening from outside of the vessel. The method may include securing the internal and external sealing members together with the at least one suture member to seal closed the vascular opening. The plurality of needles may include first and second pairs of needles, and the at least one suture member includes first and second suture members that each include first and second ends that are drawn through the vessel wall. Drawing the first and second ends of the at least one suture member through the vessel wall may include pulling the first and second ends of the at least one suture member through separate holes in the vessel wall formed by the plurality of needles.

The foregoing and other features, utilities, and advantages of the invention will be apparent from the following detailed description of the invention with reference to the accompanying drawings.

BRIEF DESCRIPTION OF THE DRAWINGS

FIGS. 20A-I illustrate a plurality of internal sealing member embodiments each including a plurality of suture openings.

FIGS. 21A-F illustrate a plurality of external sealing member embodiments each including at least one suture opening.

DETAILED DESCRIPTION

Figure 1:
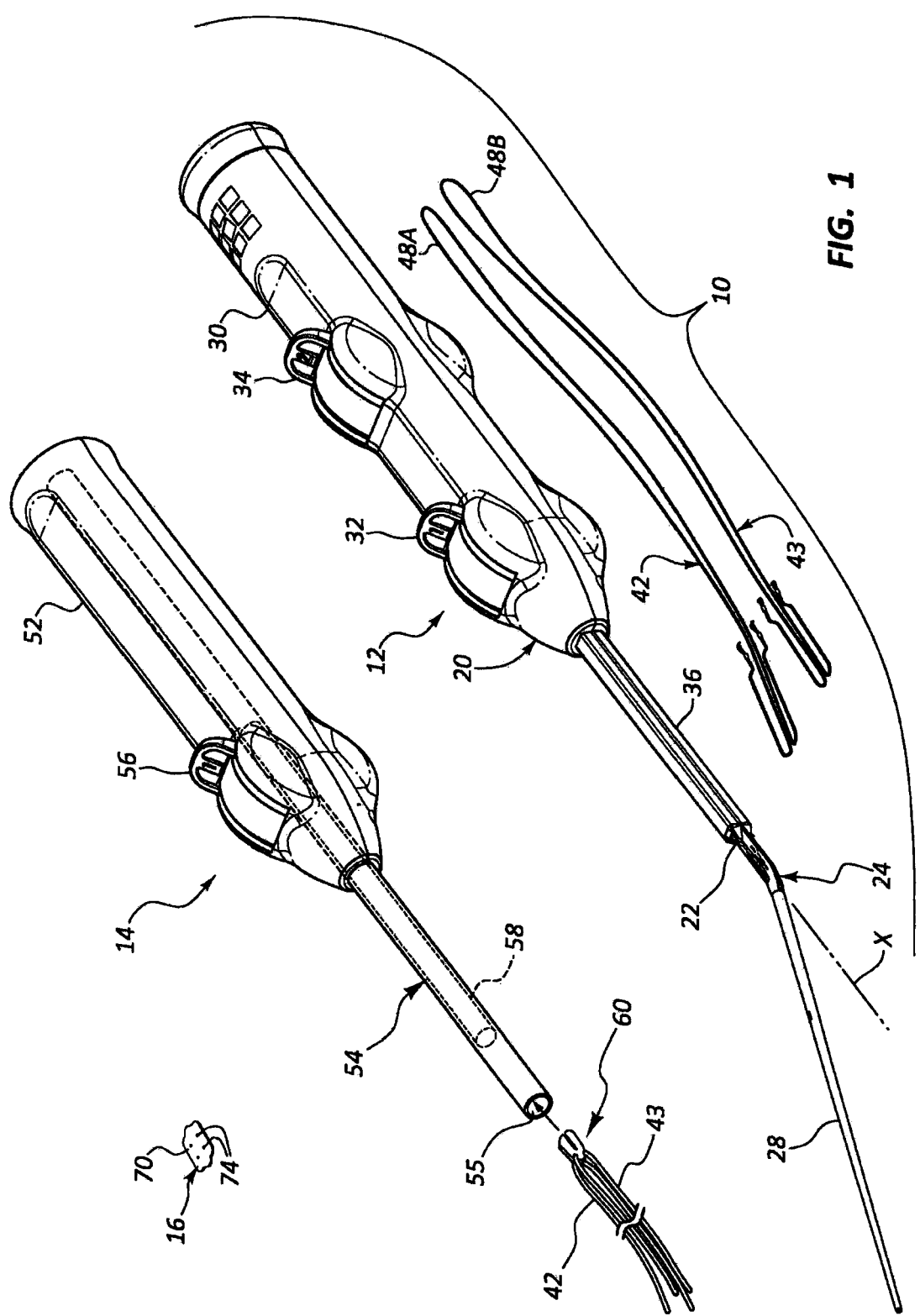
FIG. 1 is a perspective view of an example vascular closure system in accordance with the present disclosure.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

As used in this specification and the appended claims, the terms "compact," "compaction," and "compacting" are used broadly to mean packing down and compressing by one or a succession of blows or taps or smooth, steady pressure, but not by excessive force. The terms "tamp" and "tamping" may relate to certain types or forms of "compaction" and "compacting." "Engage" and "engagable" are also used broadly to mean interlock, mesh, or contact between two devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc. While the vascular instruments shown and described below include puncture closure devices, the application of principles described herein are not limited to the specific devices shown. The principles described herein may be used with any medical device. Therefore, while the description below is directed primarily to arterial procedures and certain embodiments of a tissue puncture closure device, the methods and apparatus are only limited by the appended claims.

The present disclosure is directed to a device that places at least one suture across a wound (e.g., a puncture in a vessel) and seals closed the wound. In one embodiment, the device is adapted and configured to place a pair of sutures across an opening in a wall of the vessel. The opening may be a large bore opening sized at least 10 French. The present disclosure contemplates that a medical procedure will be performed through a sheath that is inserted through the opening in the vessel wall. The sheath provides access to the inside of the vessel. At least some functions of the device may be used prior to the sheath being inserted through the opening (e.g., positioning the sutures through the vessel wall), while other functions of the device may be completed after the sheath is removed (e.g., sealing closed the vessel opening). The device deploys at least one suture across the vessel opening by inserting a plurality of needles through the vessel wall adjacent to the opening. The needles grasp lengths of suture held by the device that are positioned within the vessel, and withdrawing the needles pulls the lengths of suture through the vessel wall. The sutures, in combination with at least one sealing member, may be subsequently used to close the opening.

In one embodiment, a first or internal sealing member is advanced along the sutures to a position within the vessel. The sutures are used to secure the first sealing member in contact against an inner surface of the vessel. The internal sealing member may at least partially cover the vessel opening. A second or external sealing member may be advanced along the sutures to a position external the vessel and in contact with an outer surface of the vessel. The sutures may be used to secure the external sealing member in position to at least partially cover and seal the vessel opening. In some arrangements, the internal and external sealing members may be secured together using the sutures. In some arrangements, a separate suture may be used to secure the external sealing member in place. A tamping member or other structure may be used to compact the external sealing member against the vessel opening to provide improved sealing of the vessel opening. At least one suture may be used to retain the external sealing member in a compacted position.

In one example, the free ends of a suture extend through punctures on opposing sides of a vessel opening, and a continuous loop of the same suture extends back through the vascular opening. The internal sealing member is attached to the continuous loop portion of the suture and delivered, along with the continuous loop portion of the suture, through the vascular opening to a position within the vessel. The free ends of the suture are then pulled away from the vascular opening to draw the internal sealing member into contact with an inner surface of the vessel adjacent to and at least partially covering the vascular opening. The external sealing member may then be advanced along the sutures to a position contacting an external surface of the vessel to assist in further sealing closed the vascular opening.

The internal and external sealing members may include a plurality of suture openings through which at least one suture passes to assist in connecting the sealing members to the vessel wall. A single suture may extend through a plurality of openings in the vessel wall and a plurality of openings in at least one of the sealing members. In some arrangements, two separate sutures are used to secure the sealing members to the vessel wall and to each other. Each suture may pass through a plurality of openings in the vessel wall and a plurality of openings in at least one of the sealing members.

The internal and external sealing members may be configured to move between expanded and contracted configurations. In a contracted configuration, the sealing members may be inserted into a delivery device that assists in delivering the sealing member through a tissue tract of the vessel to the vascular opening. In the case of the internal sealing member, the delivery device may also be advanced through the vascular opening into the vessel to position the internal sealing member within the vessel. In the expanded configuration, the sealing member may provide increased surface area for contact with either the inner or outer surface of the vessel to provide improved sealing and/or anchoring functions.

Referring now to FIG. 1, an example vascular closure system 10 is shown and described. The vascular closure system 10 includes a suture delivery device 12, an internal sealing member device 14, and an external sealing member device 16. Each of the components of the vascular closure system 10 may be used individually to provide a particular function such as, for example, the suture delivery function of the suture delivery device 12, positioning of an internal sealing member using the internal sealing member device 14, or positioning of an external sealing member using the external sealing member device 16. When used in combination, the components of the vascular closure system 10 may provide an improve closure and sealing of a vascular opening. While the vascular closure system 10 is described herein for use in sealing a vascular puncture in an internal vessel that is accessible through an incision in the skin, the general principles disclosed herein may be used for closure of an incision in any tissue separating two internal portions of a living body such as, for example, punctures or incisions in blood vessels, ducts or lumens, gallbladders, livers, hearts, etc.

The suture delivery device 12 is shown and described in further detail with reference to FIGS. 1-9. The suture delivery device 12 includes an insertion member 20, an anchor member 22, a suture carrying portion 24, needles 26, and a locator tip 28. In operation, the insertion member 20 advances the anchor 22, suture carrying portion 24 and locator tip 28 through a vessel puncture 84 in a vessel wall 82 and into a vessel lumen 86 of a vessel 80 (see FIGS. 3-9. The suture delivery device 12 operates to expand the anchor 22 and to capture the vessel wall 82 prior to advancing the needles 26 through the vessel wall 82. Further operation of the suture delivery device 12 includes withdrawing the needles 26 to draw a plurality of suture ends through the vessel wall 82.

Figure 2:
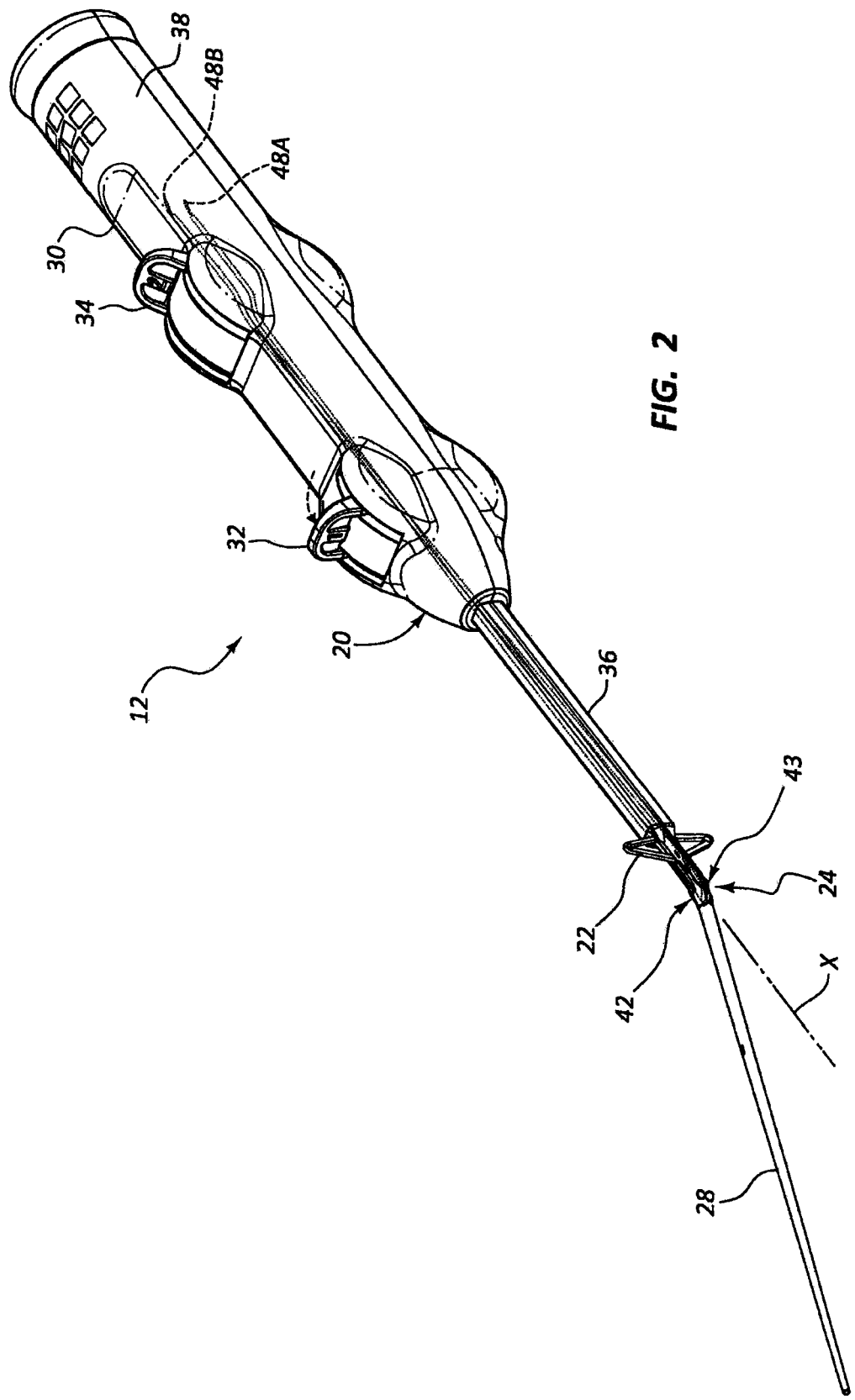
FIG. 2 is a perspective view of a suture delivery device of the vascular closure system of FIG. 1.

The insertion member 20 includes a handle 30, first and second actuators 32, 34, a distal end 36, and a hollow interior 38 (see FIG. 2). The first actuator 32 operates to expand and retract the anchor 22, and to withdraw the anchor 22 to capture and orient a portion of the vessel wall 82. The second actuator 34 operates to advance and retract the needles 26. Various operational components of the insertion member 20 are positioned within the hollow interior 38. Portions of the sutures may also be positioned within the hollow interior 38. For example, loop portions of 48A, 48B of the sutures may be positioned within the hollow interior 38 to help maintain the loop portions outside of the vessel during operation of the suture delivery device 12.

The first and second actuators 32, 34 may rotate between various operational positions. The first and second actuators 32, 34 may be positioned at axially spaced apart locations along the handle 30 for easy thumb or finger manipulation by the user.

The distal end 36 is typically inserted through an incision tract (e.g., tissue tract) in order to access the vascular opening of a vessel. The vascular opening may be accessible percutaneously and may be referred to as a percutaneous tissue puncture.

The anchor 22 may be operated between a retracted position (see FIGS. 1 and 3) and an extended or expanded position (see FIGS. 2 and 4-7A). In addition to expanding radially outward, the anchor 22 may also move axially to capture the vessel wall 82 between the anchor 22 and the distal end 36. Capturing a portion of the vessel wall 82 may also include arranging a portion of the vessel wall 82 generally perpendicular to a longitudinal axis X of the suture delivery device 12. Arranging a portion of the vessel wall 82 generally perpendicular to the longitudinal axis X may improve ease of insertion of the needles 26 through the vessel wall 82, and may provide improved uniformity in spacing of a puncture location for the needles 26 relative to the vessel puncture 84 during insertion of needles 26.

The anchor 22 may remain in a retracted position during insertion of the anchor 22 through the vessel puncture 84. The anchor 22 may be moved into an expanded position and withdrawn axially during advancing and withdrawal of the needles 26. The anchor 22 may be moved to the retracted position prior to removal of the insertion member 20 from the vessel puncture 84.

The suture carrying portion 24 may include a plurality of suture connectors 40, and first and second sutures 42, 43 each having first and second suture ends 44, 46 and one of the suture loops 48A, 48B. A separate suture connector 40 may be connected or mounted to each of the first and second suture ends 44, 46. The suture connectors 40 may be positioned distally of the anchor 22. In operation, the needles 26 extend through the vessel wall 82 and into contact with the suture connectors 40 to provide a connection between the needles 26 and the first and second suture ends 44, 46 of each of the first and second sutures 42, 43. Withdrawal of the needles 26 draws the suture connectors 40 and first and second suture ends 44, 46 through needle openings 88 defined by the needles 26, and into the insertion member 20. Removal of the suture delivery device 12 from the vessel puncture 84 pulls the first and second sutures 42, 43 through the vessel wall 82 and to a location exterior of the vessel 80.

Figure 9:
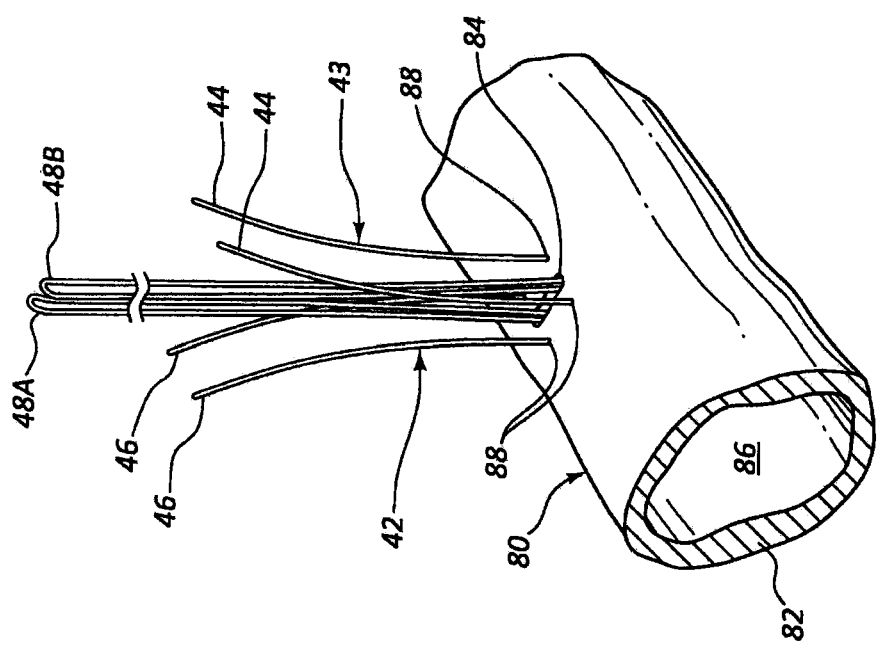
FIG. 9 shows a position of the sutures after removal of the suture delivery device from the vessel.

A suture loop 48A, 48B extends between the first and second ends 44, 46 of each of the first and second sutures 42, 43, respectively. The suture loops 48A, 48B may extend into the insertion member 20, for example, through the distal end 36 and into the handle 30. The suture loops 48A, 48B extend through the vessel puncture 84 and to a location exterior of the vessel 80 wherein the operator has access to the suture loops 48A, 48B. FIG. 9 illustrates an arrangement for the first and second sutures 42, 43 after operation of the suture delivery device 12 to position the first and second suture ends 44, 46 extending through the vessel wall 82, and the suture loops 48A, 48B extending through the vessel puncture 84 and being accessible outside of the vessel 80.

The locator tip 28 may extend distally from the suture carrying portion 24. The locator tip 28 may be flexible and pliable to assist in inserting the insertion member 20 through the vessel puncture 84 and into the vessel lumen 86. The locator tip 28 may have various shapes and sizes, including different lengths.

An example suture delivery device is disclosed in U.S. Patent Application No. 61/494,345, filed on 7 Jun. 2011, and entitled "Large Bore Closure Device and Methods," which application is incorporated herein in its entirety by this reference. The suture delivery device 12 of the present application provides for positioning of the suture loops 48A, 48B through the vessel puncture 84 upon completing operation of the suture delivery device 12.

Figure 10:
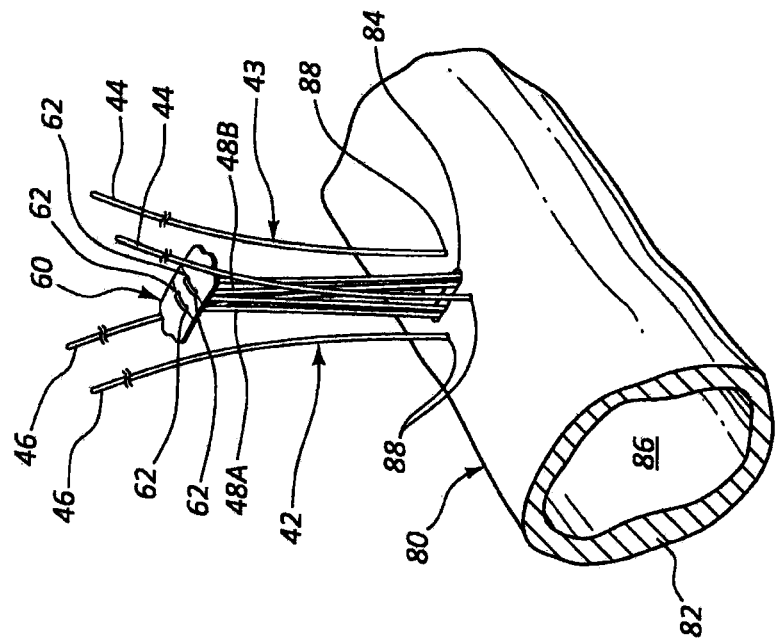
FIG. 10 is a perspective view showing an internal sealing member connected to the sutures.
Figure 11:
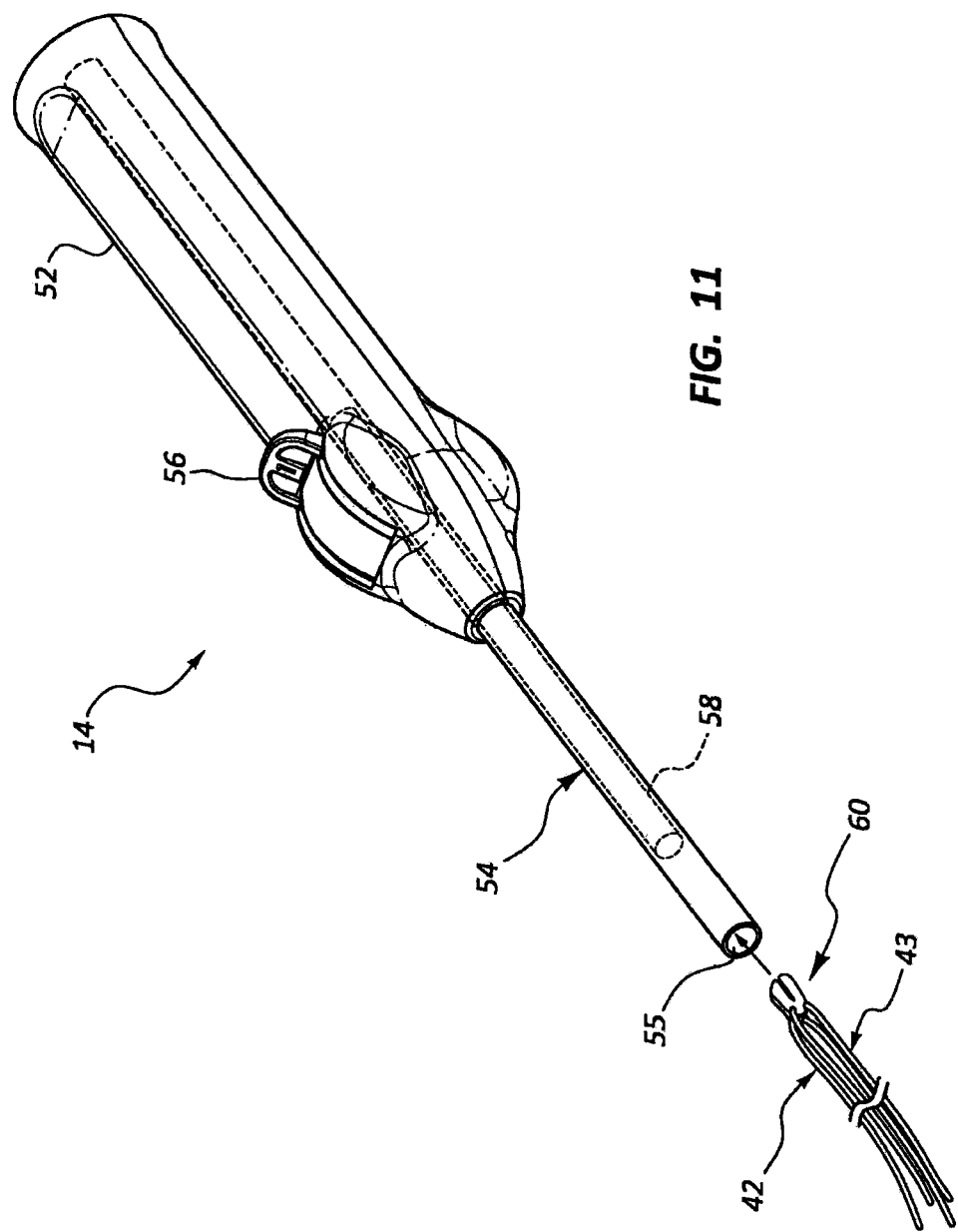
FIG. 11 shows an internal sealing member device of the vascular closure system of FIG. 1.

Referring now to FIGS. 10-15, the internal sealing member device 14 may include a handle 52, a carrier tube 54 having a distal end 55, an actuator 56, an advancing member 58, and an internal sealing member 60 (see FIG. 11). The actuator 56 may rotate between various positions to advance or retract the advancing member 58 within the carrier tube 54. Advancing the advancing member 58 expels the internal sealing member 60 from the distal end 55 of the carrier tube 54. The advancing member 58 may be in the form of a tube or other structure that applies an axially-directed force on the internal sealing member 60.

The internal sealing member 60 may include a plurality of suture openings 62. The suture openings 62 may receive the suture loops 48A, 48B. In some arrangements, the operator manually attaches the internal sealing member 60 to the suture loops 48A, 48B after the sutures 42, 43 have been positioned across the vessel puncture 84 (e.g., using the suture delivery device 12) and before positioning the internal sealing member 60 within the internal sealing member device 14. Alternatively, the internal sealing member 60 may be connected to the sutures 42, 43 as part of assembling the suture delivery device 12 and carried within the suture delivery device 12 until being expelled from suture delivery device 12 after positioning the sutures 42, 43 across the vessel puncture 84. In some arrangements, the suture loops 48A, 48B are positioned extending through the suture openings 62 prior to operation of the suture delivery device 12 to draw the first and second suture ends 44, 46 through the vessel wall 82 adjacent to the vessel puncture 84. The internal sealing member 60 may be positioned within the carrier tube 54 for delivery into the vessel 80 while the suture loops 48A, 48B remain extending through the suture openings 62.

Figure 13:
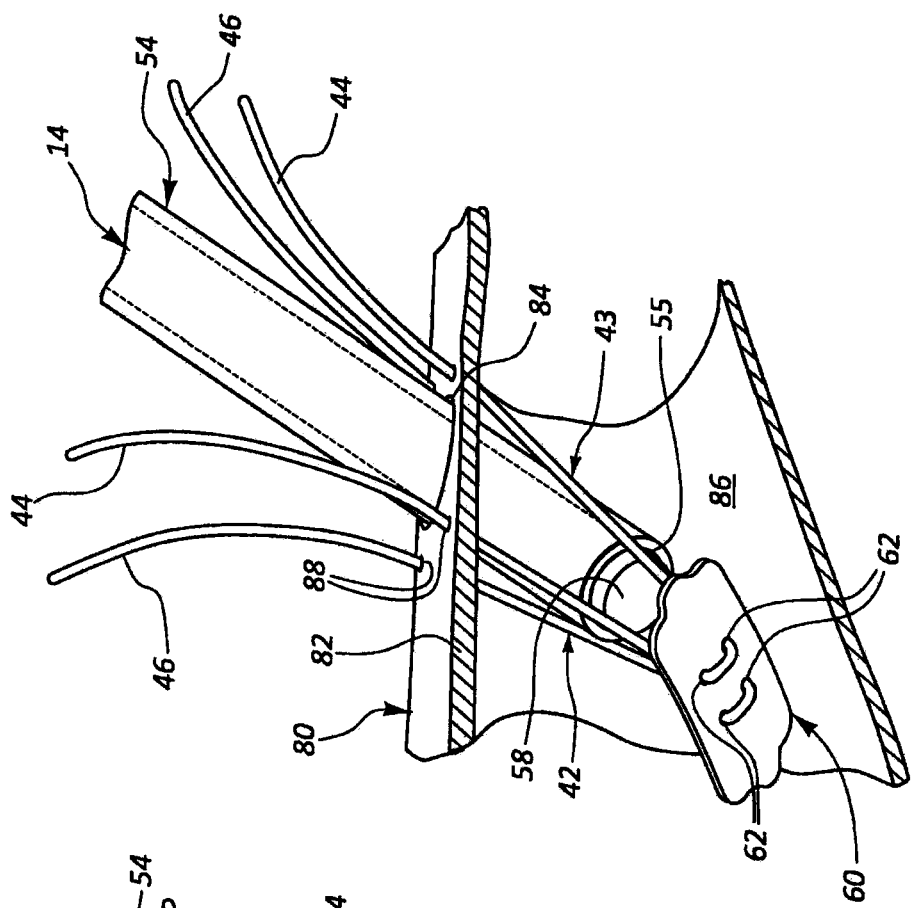
FIG. 13 is a perspective view showing the internal sealing member of the internal sealing member device of FIG. 12 disposed within the vessel.
Figure 12:
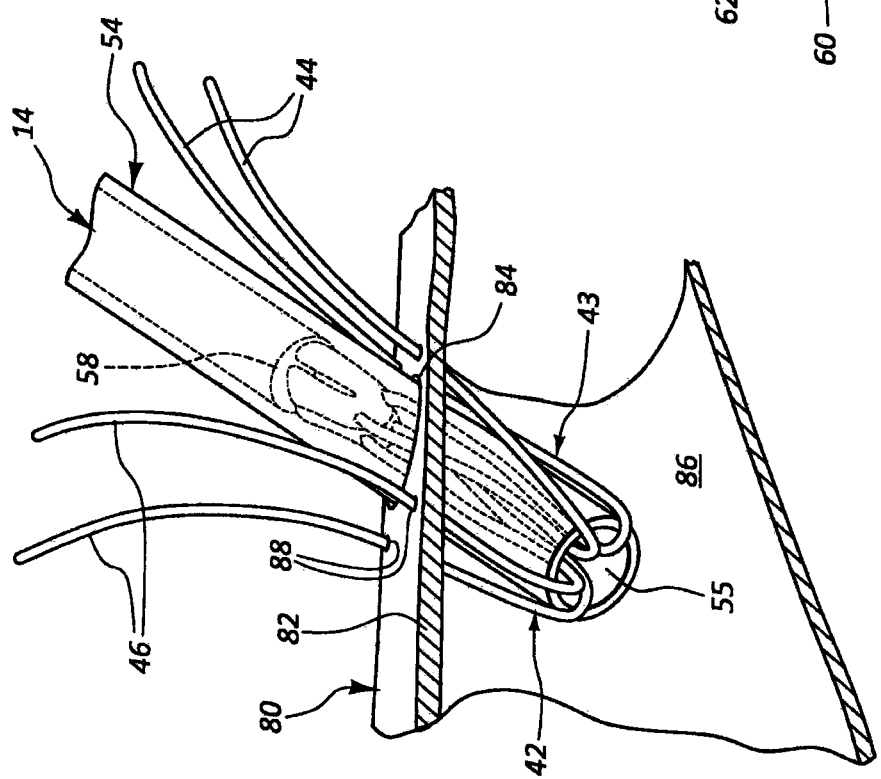
FIG. 12 is a perspective view showing the internal sealing member device of FIG. 11 inserted into the vessel of FIG. 10.
Figure 15:
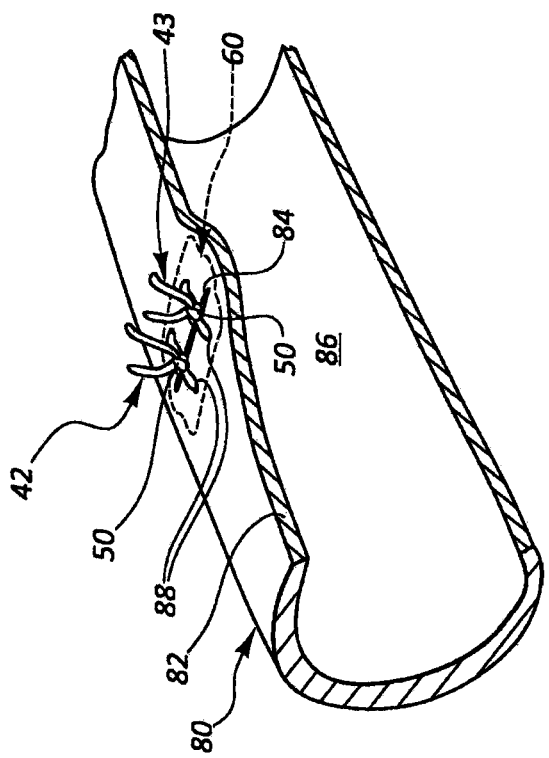
FIG. 15 is a perspective view showing the internal sealing member of FIG. 14 secured within the vessel with the sutures.
Figure 14:
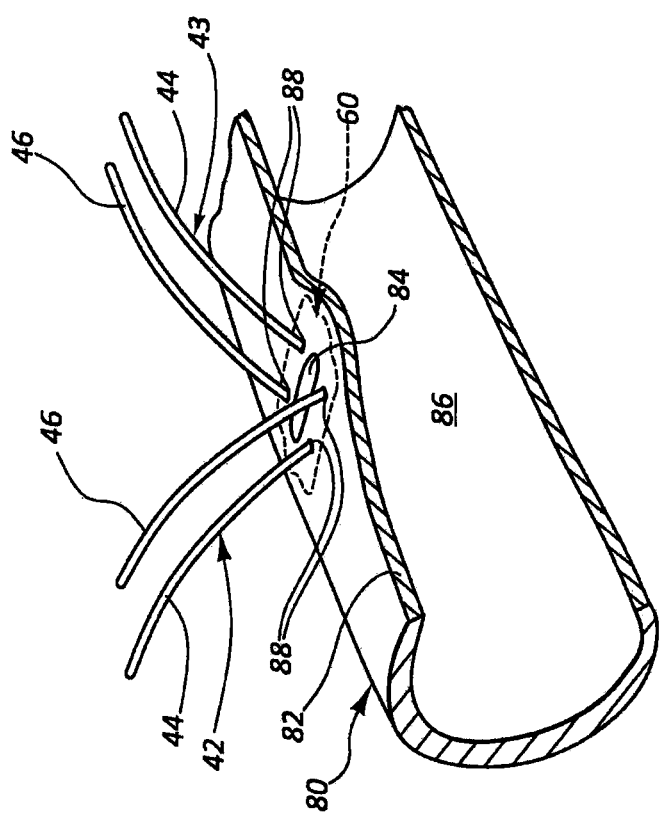
FIG. 14 is a perspective view showing the internal sealing member positioned against the vessel wall adjacent to the vascular opening.

The internal sealing member 60 may be held in a compacted position (e.g. folded, rolled or compressed) prior to being positioned within the carrier tube 54. The carrier tube 54 holds the internal sealing member 60 in the compacted position for improved ease in inserting the internal sealing member 60 through the vessel puncture 84. FIG. 12 shows the carrier tube 54, which has the internal sealing member 60 positioned therein, advanced through the vessel puncture 84 and into the vessel lumen 86. The first and second sutures 42, 43 extend out of the distal end 55 of the carrier tube 54 and through the needle openings 88. FIG. 13 shows the internal sealing member 60 expelled from the carrier tube 54 by advancing the advancing member 58. Further withdrawing the first and second ends 44, 46 of the first and second sutures 42, 43 draws the internal sealing member 60 against an internal surface of the vessel 80 as shown in FIG. 14. The internal sealing member 60 may be retained in this position contacting the internal surface of the vessel 80 and at least partially covering the vessel puncture 84 by tying a plurality of knots 50 in the first and second sutures 42, 43 as shown in FIG. 15. The vessel puncture 84 may be drawn closed and maintained in a closed position using the suture knots 50.

Figure 17:
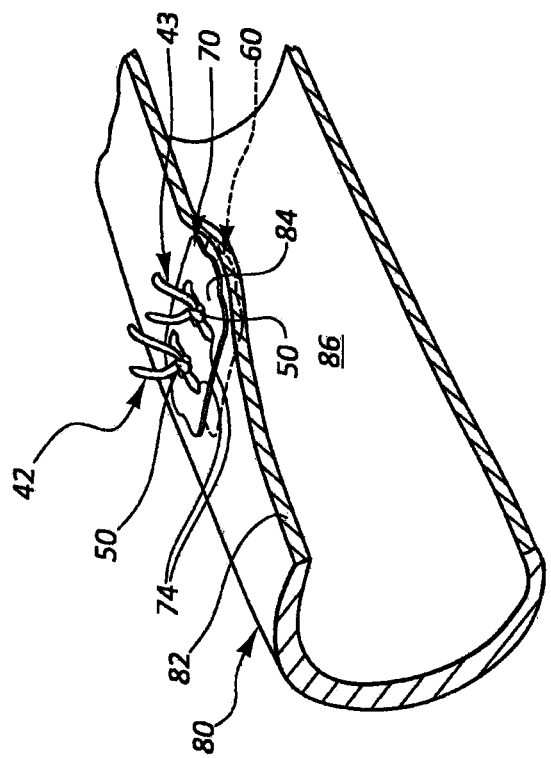
FIG. 17 shows the external sealing member of FIG. 16 secured in place with the sutures.
Figure 16:
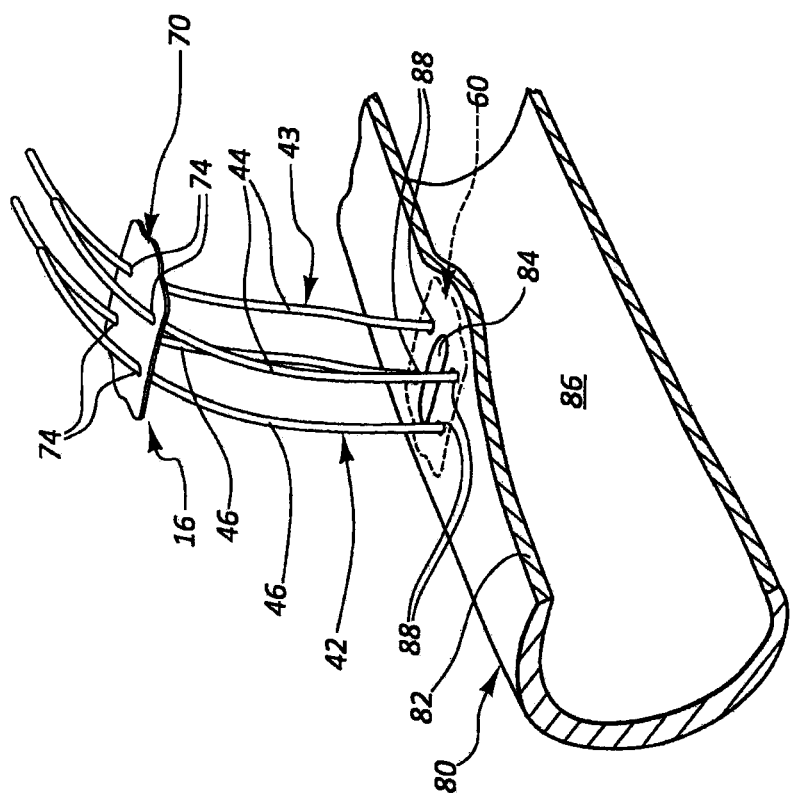
FIG. 16 is a perspective view showing an external sealing member being advanced over the sutures to the vascular opening.

Alternatively, or in addition to forming the suture knots 50 as shown in FIG. 15, the external sealing member device 16 may be used to further seal closed the vessel puncture 84 and retain the internal sealing member 60 in place within the vessel 80. Referring to FIGS. 16-17, the external sealing member device 16 may include an external sealing member 70 that is advanced along the first and second sutures 42, 43 into contact with an external surface of the vessel 80. The external sealing member 70 may include a plurality of suture openings 74 through which the first and second sutures 42, 43 extend. The first and second sutures 42, 43 may be advanced through the suture openings 74 manually by the operator (e.g., during the procedure by, for example, threading the first and second sutures 42, 43 through the suture openings 74). Alternatively, the external sealing member 70 may be attached to the sutures 42, 43 automatically by operation of one of the suture delivery device 12 and internal sealing member device 14 (e.g., by advancing the needles 26 of suture delivery device 12 through the external sealing member 70 when positioning the sutures 42, 43 across vessel puncture 84). The external sealing member 70 may be advanced along the first and second sutures 42, 43 to a position contacting the external surface of the vessel 80 as shown in FIG. 17. The external sealing member 70 may be retained in place by tying a plurality of suture knots 50 in the first and second sutures 42, 43. The vessel puncture 84 may be drawn into a closed position at the time of forming the suture knots 50. Tying the suture knots 50 may also provide a connection between the internal sealing member 60 and external sealing member 70. A portion of the vessel wall 82 may be sandwiched or secured between the internal and external sealing members 60, 70. Other types of fastening devices or structures may be used in place of the suture knots 50 to maintain tension in the first and second sutures 42, 43 as part of sealing closed the vessel puncture 84 and connecting the internal and external sealing members 60, 70 to each other and to the vessel wall 82.

Figure 19:
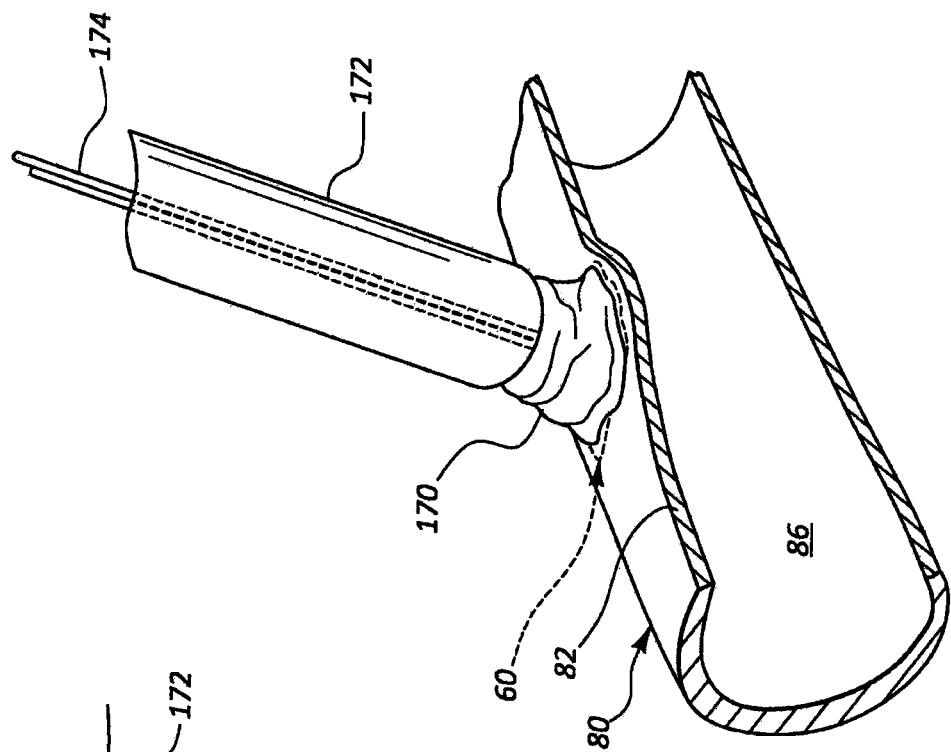
FIG. 19 is a perspective view showing the external sealing member device being operated to compact the external sealing member to seal closed the vascular opening.
Figure 18:
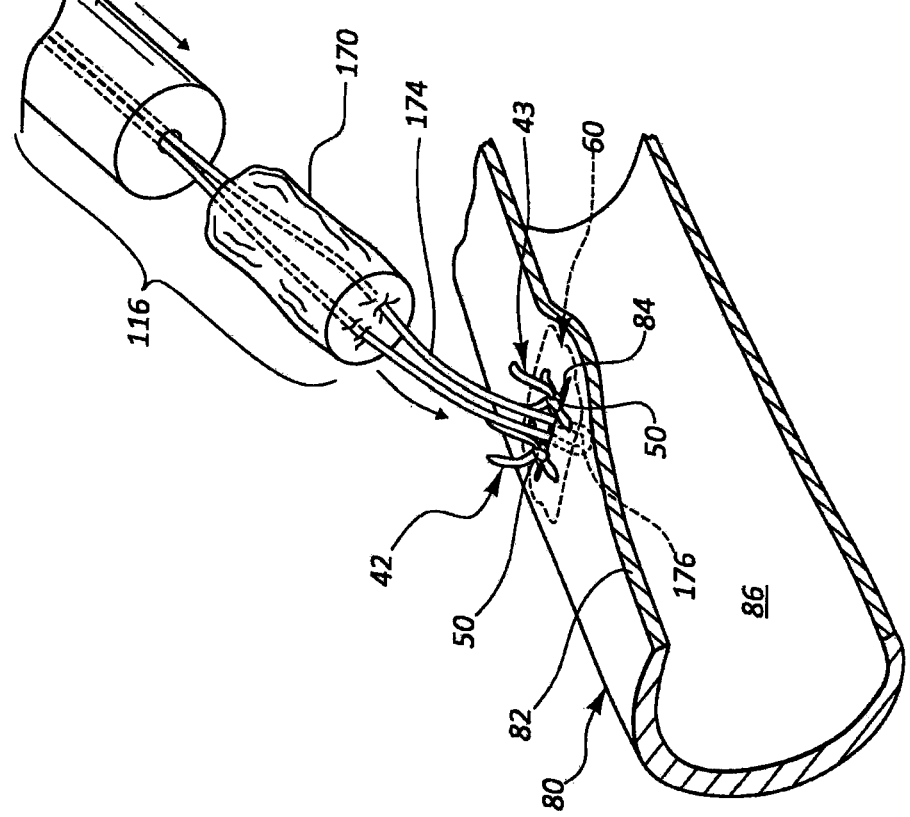
FIG. 18 is a perspective view showing another example external sealing member device having an external sealing member and a compaction member being advanced along a suture to the vascular opening.

Referring to FIGS. 18 and 19, an alternative external sealing member device 116 is shown and described. The external sealing member device 116 includes an external sealing member 170, a compaction member 172, and a secondary suture 174. The secondary suture 174 may be connected to the internal sealing member 60. Alternatively, the secondary suture 174 may be connected to the vessel wall 82. The secondary suture 174 may be secured with a suture connection 176. In some arrangements, the secondary suture 174 is embedded in or permanently connected in some other way to the internal sealing member 60. The secondary suture 174 may be connected to the internal sealing member 60 prior to positioning the internal sealing member 60 within the vessel 80.

The external sealing member device 116 may be part of a vascular closure device that helps deliver the external sealing member 170 to a position adjacent to a vessel puncture 84, and compacts the external sealing member 170 with the compaction member 172. In some arrangements, the vascular closure device, which includes the external sealing member device 116, may automatically compact the external sealing member 170 with the compaction member 172 upon application of a withdrawal force to the vascular closure device. One example of such vascular closure device is shown and described in U.S. Pat. No. 7,618,438, entitled "Tissue Puncture Closure Device With Disengageable Automatic Tamping System," which patent is incorporated herein in its entirety by this reference.

FIG. 19 shows the external sealing member 170 being compacted against the external surface of the vessel 80 with the compaction member 172. The external sealing member 170 may help seal closed the vessel puncture 84. The internal sealing member 60 may be used as an anchor while applying the compaction force applied by the compaction member 172. A fastener, locking member, or knot may be positioned proximal of the compacted external sealing member 170 to maintain the external sealing member 170 in the compacted state shown in FIG. 19.

Referring to FIGS. 20A-I, a plurality of internal sealing member embodiments are shown and described. The internal sealing members 60A-I each include a plurality of suture openings 62A-I (including 62G' and 62I'). The suture openings 62A-I may have different shapes and sizes such as, for example, circular, oval, or rectangular, and may be constructed as an elongate slot. Suture openings of different shapes and sizes may be combined on a single internal sealing member. Each of the internal sealing members 60A-I may have a different shape and size. For example, the internal sealing member 60A, 60D, 60G, 60H each have a generally rectangular shape, while the internal sealing members 60B, 60E, 60I have a generally oval shape, and internal sealing members 60C, 60F have a generally circular shape. Many other shapes and sizes are possible, and additional features may be included on any one of the internal sealing members 60A-I.

In one example, the internal sealing member 60H includes a guidewire opening 66. The guidewire opening 66 may permit passage of a guidewire through the internal sealing member 60H during placement and operation of the internal sealing member device 14. Alternatively, the guidewire opening 66 may act as an opening through which the secondary suture 174 of the external sealing member device 116 extends to provide a connection internal of the vessel 80. The guidewire opening 66 may include a plurality of openings through which one or more strands of suture extend and to provide a structure for improved ease in connecting a suture to the internal sealing member 60H.

Referring to FIGS. 21A-F, a plurality of external sealing member embodiments 70A-F are shown. The external sealing member 70A-F may have different shapes, sizes, and numbers of suture openings 74A-F. Each external sealing member 70A-F may include one or more suture openings 74A-F. The suture openings 74A-F may have different sizes and shapes, including different sizes or shapes on a single external sealing member 70A-F. For example, external sealing member 70F shown in FIG. 21F includes suture opening 74 having a generally circular shape, and suture opening 74F' has an elongate oval or slot shape.

The external sealing members 70A-F may also include a guidewire opening 76 (see FIG. 21D). The guidewire opening 76 may be configured to permit passage of a guidewire through the external sealing member 70D during delivery of the external sealing member 70 to a position adjacent to or in contact with the vessel 80. Alternatively, the guidewire opening 76 may permit passage of at least one additional suture member, and may include a plurality of additional suture openings.

The external sealing member 70 may have various shapes and sizes in addition to the generally oval, elongate shape shown in FIGS. 21A and 21C-F, and the generally circular shape of FIG. 21B. Other shapes include, for example, rectangular, square, hexagonal, and triangular.

The external sealing members 70A-F may be compacted or temporarily reduced in size prior to being advanced to the vessel puncture 84. For example, a device such as the internal sealing member device 14, which includes a handle, carrier tube, actuator, and advancing member may hold the external sealing member in a compacted state during delivery and then expel the external sealing member adjacent to the vessel where the external sealing member expands prior to being secured to the vessel and internal sealing member.

The internal and external sealing members 60, 70 may comprise a bioresorbable material or a biocompatible material. The structure of the internal and external sealing members 60, 70 may be generally flexible, or alternatively, be generally rigid or include rigid portions. In one example, the internal sealing member 60 includes a suture secured to or embedded within it to facilitate placement and securing of the external sealing member 70.

Figure 3:
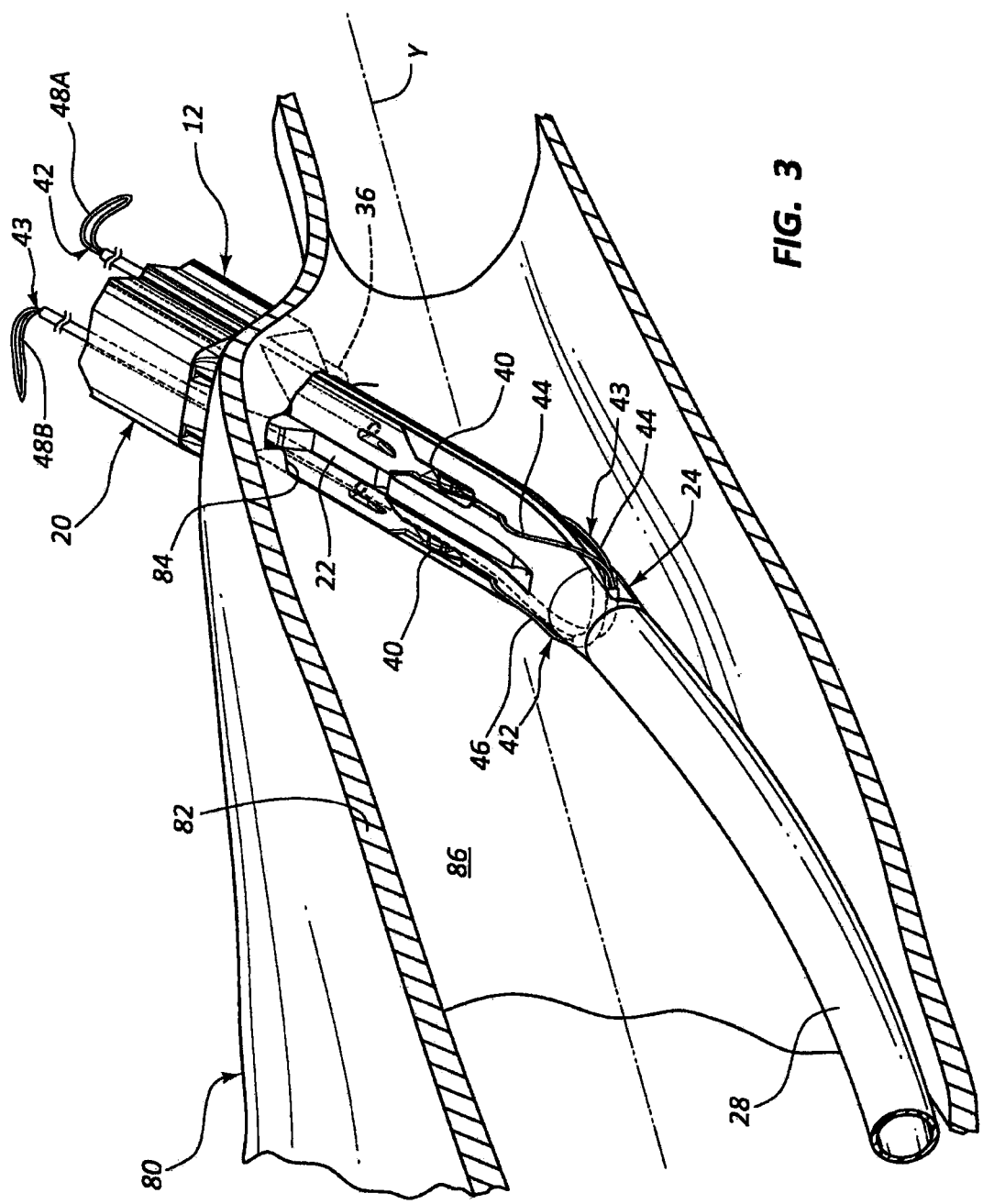
FIG. 3 is a perspective view of a portion of the suture delivery device of FIG. 2 inserted into a vessel.
Figure 4:
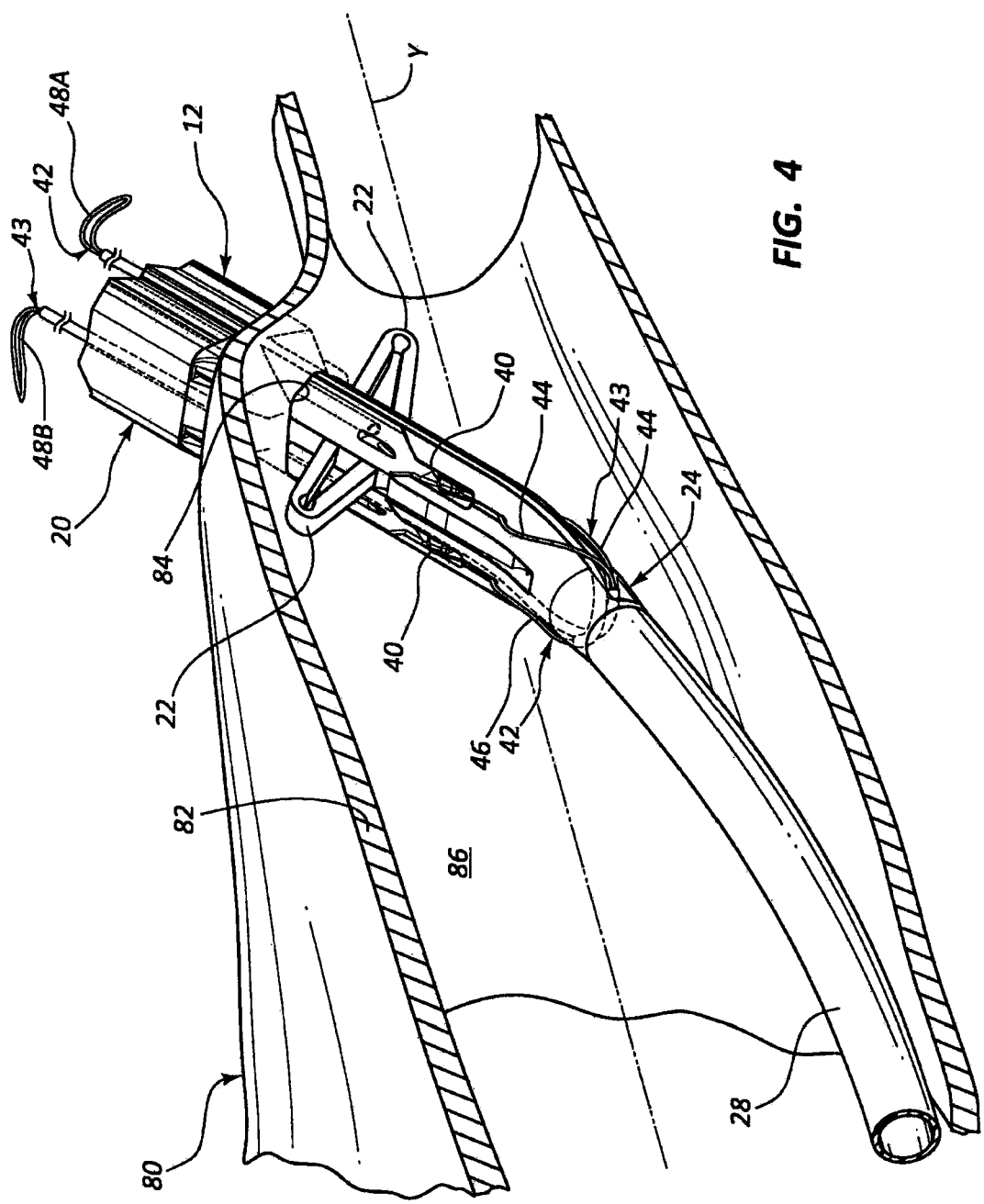
FIG. 4 is a perspective view showing the suture delivery device of FIG. 3 with an anchor deployed.
Figure 5:
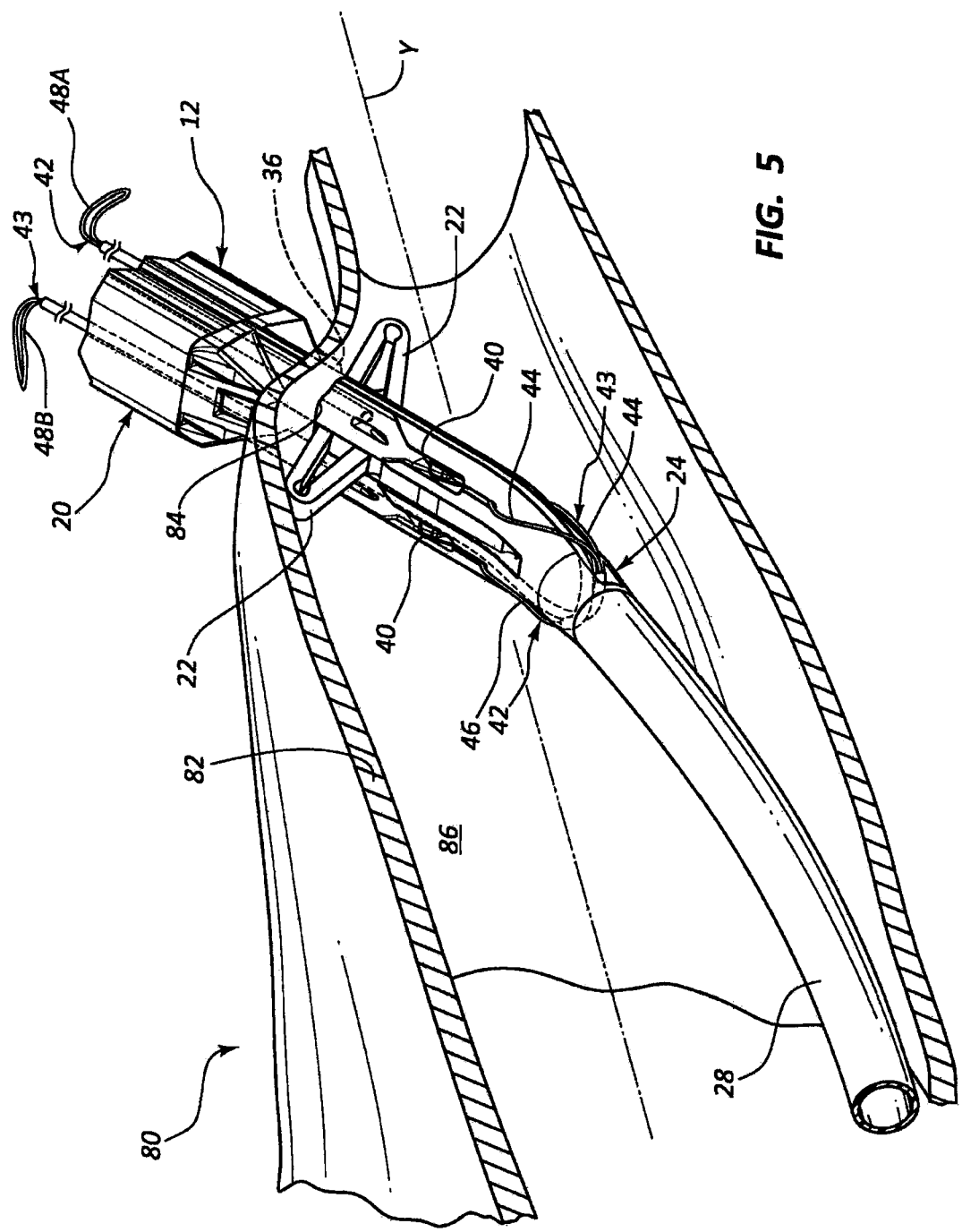
FIG. 5 is a perspective view of the suture delivery device of FIG. 4 with a portion of the vessel wall captured by the anchor.
Figure 6:
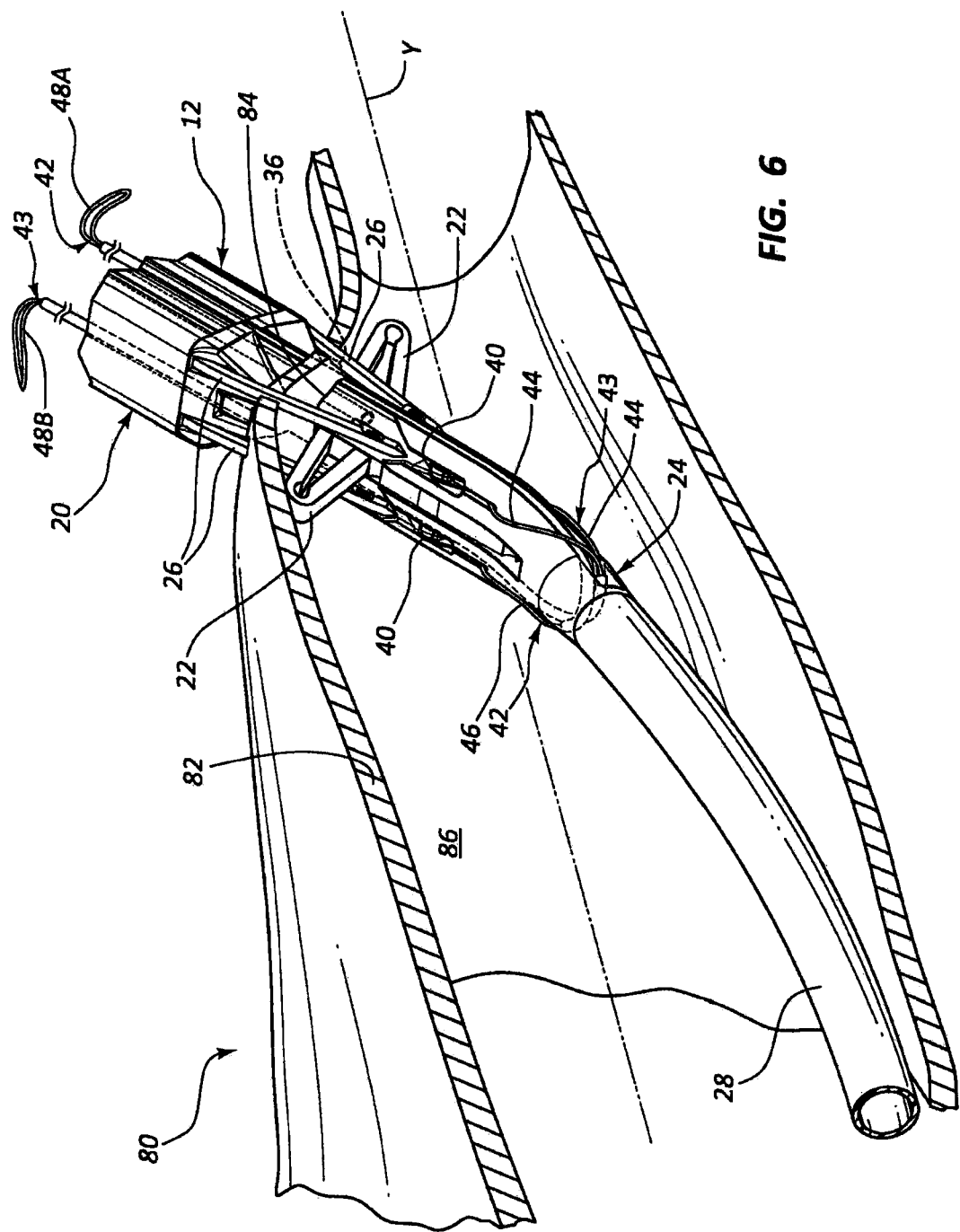
FIG. 6 is a perspective view of the suture delivery device of FIG. 5 with a plurality of needles penetrating the vessel wall.
Figure 7:
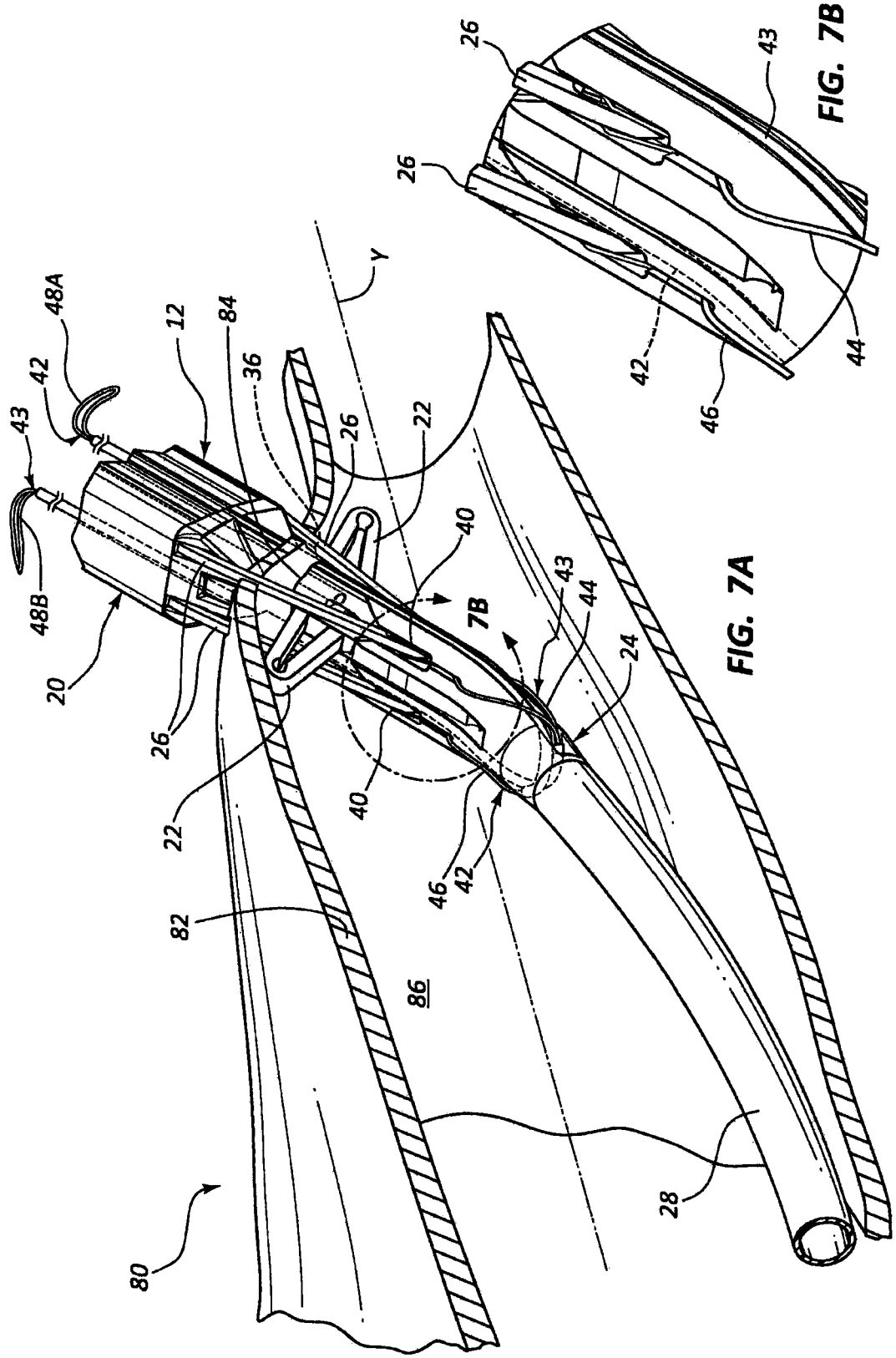
FIGS. 7A and 7B are perspective views showing the suture delivery device of FIG. 6 connecting the plurality of needles with sutures carried by the suture delivery device.

Referring again to FIGS. 3-17, a method of operating the vascular closure system 10 is described in further detail. The method may begin with inserting a guidewire through the vessel puncture 84 and into the vessel lumen 86. The suture delivery device 12 is advanced over the guidewire through the vessel puncture 84 and into the vessel lumen 86 as shown in FIG. 3. The first actuator 32 is operated to move the anchor 22 into an expanded or deployed position as shown in FIG. 4. The first actuator 32 is further operated to withdraw the anchor 22 in a proximal direction to capture a portion of the vessel wall 82 between the anchor 22 and the distal end 36 of the insertion member 20 as shown in FIG. 5. In some examples, expanding/deploying the anchor 22 concurrently captures a portion of the vessel wall 82. The second actuator 34 is operated to advance the needles 26 through the vessel wall 82 as shown in FIG. 6. Further advancing the needles 26 provides a connection of the needles 26 to the suture connectors 40 as shown in FIGS. 7A and 7B.

Figure 8:
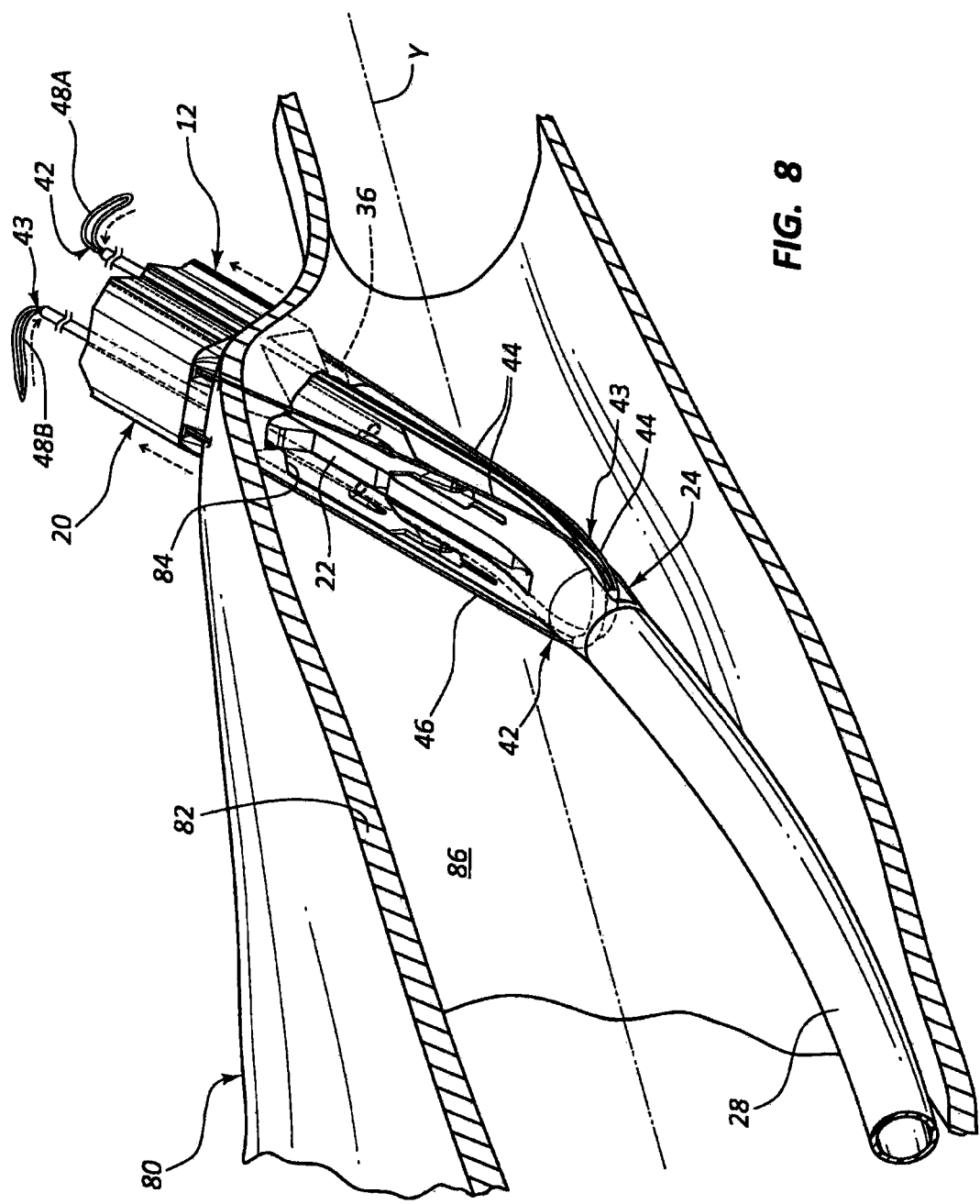
FIG. 8 is a perspective view of the suture delivery device of FIGS. 7A-B with the plurality of needles withdrawn to draw the sutures through the vessel wall.

The second actuator 34 is then operated to withdraw the needles 26 back through the vessel wall 82 (via the needle openings 88) to withdraw the suture connectors 40 and first and second suture ends 44, 46 of each of the first and second sutures 42, 43 through the vessel wall 82 and into the insertion member 20 as shown in FIG. 8. The first actuator 32 is operated to move the anchor 22 into the retracted position as shown in FIG. 8. The suture delivery device 12 is then withdrawn proximally from the vessel puncture 84 and the first and second suture ends 44, 46 and suture loops 48A, 48B are removed from the suture delivery device 12 as shown in FIG. 9.

The first and second sutures, 42, 43 extend through the needle openings 88 at locations radially spaced outward from the vessel puncture 84 to be spaced apart and adjacent to the vessel puncture 84. A portion of the first and second sutures (e.g., the suture loops 48A, 48B) extend through the vessel puncture 84. The first and second suture ends 44, 46 and suture loops 48A, 48B are positioned outside of the vessel 80 and accessible by the operator.

Referring now to FIG. 10, the internal sealing member 60 is connected to the suture loops 48A, 48B. The internal sealing member 60 may include slots or other features that provide access to the suture openings 62 from a peripheral edge of the internal sealing member 60. Alternatively, the first and second sutures, 42, 43 may be threaded through the internal sealing member 60 prior to operating the suture delivery device 12 to draw the first and second sutures 42, 43 through the needle openings 88 in the vessel wall 82.

Referring now to FIG. 11, the internal sealing member 60 with suture loops 48A, 48B threaded there through is positioned within the carrier tube 54 of the internal sealing member device 14. The carrier tube 54 is advanced through the vessel puncture 84 to position the internal sealing member 60 within the vessel lumen 86 as shown in FIG. 12. The actuator 56 of the internal sealing member device 14 is operated to advance the advancing member 58 to expel the internal sealing member 60 within the vessel lumen 86 as shown in FIG. 13. The carrier tube 54 is withdrawn from the vessel puncture 84 and tension is applied to the first and second sutures 42, 43 to move the internal sealing member 60 into contact with an internal surface of the vessel 80 as shown in FIG. 14.

The internal sealing member 60 may be retained in contact with an internal surface of the vessel 80 and at least partially covering the vessel puncture 84 by tying suture knots 50 in the first and second sutures 42, 43 as shown in FIG. 15. Tying the suture knots 50 may also close or at least partially close the vessel puncture 84. Other connecting or locking devices may be used in place of the suture knots 50 to maintain tension in the first and second sutures 42, 43.

In one example, the vessel puncture 84 is sealed closed prior to or after forming the suture knots 50 shown in FIG. 15 by advancing an external sealing member 70 along the first and second sutures 42, 43 and into contact with an external surface of the vessel 80 as shown in FIGS. 16 and 17. The internal and external sealing member 60, 70 may be connected together using the first and second sutures 42, 43. The first and second sutures 42, 43 may be threaded through the external sealing member 70 and advanced along the first and second sutures 42, 43 to the vessel wall 82. A portion of the vessel wall 82 surrounding the vessel puncture 84 may be compressed between the internal and external sealing members 60, 70 to help seal closed the vessel puncture 84. Applying tension in the first and second sutures 42, 43 may help close the vessel puncture 84. Tension may be maintained in the first and second sutures 42, 43 by tying suture knots 50 as shown in FIG. 17. Other types of connecting or fastening structures may be used to help maintain tension in the first and second sutures 42, 43 in place of using the suture knots 50.

In an alternative method of sealing closed the vessel puncture 84, an external sealing member device 116 may be used to advance an external sealing member 170 to the vessel puncture 84, and compact the external sealing member 170 against the vessel puncture 84 as shown in FIGS. 18 and 19. A compaction member 172 may be advanced distally to compact the external sealing member 170 against the external surface of the vessel 80 and covering the vessel puncture 84 to help seal closed the vessel puncture 84. The external sealing member device 116 may include a secondary suture 174 that is connected to the internal sealing member 60 so that the internal sealing member 60 acts as an anchor and backstop while the external sealing member 170 is compacted. The external sealing member device 116 may be operating using the first and second sutures 42, 43 in place of the secondary suture 174 to maintain an anchoring function of the internal sealing member 60. The suture knots 50 (or other structure that maintain tension in the first and second sutures 42, 43) may be utilized after operation of the external sealing member device 116. In some arrangements, the first and second sutures 42, 43 may extend through the external sealing member 170 and be used to secure the external sealing member 170 to the vessel wall 82 and/or the internal sealing member 60. FIG. 19 shows the external sealing member 170 compacted with the compaction member 172 to seal closed the vessel puncture 84.

The internal and external seating member 60, 70 may also help facilitate hemostasis. In some examples, the internal and external sealing member 60, 70 include collagen or other biocompatible, bioresorbable materials. The internal and external sealing members 60, 70 may comprise different materials and may provide different functions related to sealing of the vessel puncture 84.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention. The words "including" and "having," as used in the specification, including the claims, shall have the same meaning as the word "comprising."

What is claimed is:

1. A vascular closure system, comprising:
    a suture delivery device including:
        an anchor;
        a suture carrying portion insertable through a vessel puncture of a vessel and carrying first and second suture ends of at least a first suture member, the suture carrying portion being positioned distal to the anchor;
        a plurality of needles extendable through a wall of the vessel adjacent to the vessel puncture, the plurality of needles being configured to advance in an at least partially radially inward direction into the suture carrying portion to connect to the first and second suture ends, and withdrawal of the plurality of needles draws the first and second suture ends through the vessel wall;
        an insertion member positioned proximal to the anchor, the plurality of needles being deliverable from the insertion member proximal to the anchor, the insertion member being configured to be positioned opposite the wall of the vessel relative to the anchor when the plurality of needles are delivered;
    an internal sealing member;
    a sealing member delivery device configured to contain the internal sealing member in a reduced size configuration and to deliver the internal sealing member through the vessel puncture while in the reduced size configuration, the internal sealing member configured to advance along the first suture member through the vessel puncture and into the vessel with the first suture member being at least partially radially external to the sealing member delivery device;
    wherein applying a withdrawal force to the first and second suture ends draws the internal sealing member against an internal surface of the vessel wall, wherein the internal sealing member is configured to at least partially seal closed the vessel puncture.

2. A vascular closure system according to claim 1, further comprising an external sealing member configured to advance along the first suture member to a position contacting an outer surface of the vessel wall to at least partially seal closed the vessel puncture.

3. A vascular closure system according to claim 2, wherein the internal and external sealing members are connected together with the first suture member.

4. A vascular closure system according to claim 2, wherein the internal sealing member and external sealing member each include at least one suture hole sized to receive a portion of the first suture member.

5. A vascular closure system according to claim 2, wherein the external sealing member is compacted to seal closed the vessel puncture from outside of the vessel.

6. A vascular closure system according to claim 1, wherein the plurality of needles connect to the first suture member with at least one suture connector mounted to the first suture member.

7. A vascular closure system according to claim 1, further comprising a handle and first and second actuators mounted to the handle, the first actuator being operable to expand and retract the anchor within the vessel, and the second actuator being operable to advance and withdraw the plurality of needles.

8. A vascular closure system according to claim 1, further comprising a second suture member, wherein the plurality of needles includes two pairs of needles, and a separate one of the two pairs of needles being connecting to one of the first and second suture members.

\* \* \* \* \*